(12) United States Patent
Knott et al.

(10) Patent No.: US 8,961,871 B2
(45) Date of Patent: Feb. 24, 2015

(54) APPARATUS FOR THE STERILIZATION OF PLASTICS MATERIAL CONTAINERS BY MEANS OF MEDIUM-CONTROLLED ELECTRON BEAMS

(71) Applicant: Krones AG, Neutraubling (DE)

(72) Inventors: Josef Knott, Schierling (DE); Hans Scheuren, Regensburg (DE)

(73) Assignee: Krones AG (DE)

( * ) Notice: Subject to any disclaimer, the term of this patent is extended or adjusted under 35 U.S.C. 154(b) by 229 days.

(21) Appl. No.: 13/651,239

(22) Filed: Oct. 12, 2012

(65) Prior Publication Data

US 2013/0108504 A1    May 2, 2013

(30) Foreign Application Priority Data

Nov. 2, 2011    (DE) .......................... 10 2011 055 005

(51) Int. Cl.
*A61L 2/00*    (2006.01)
*B01D 50/00*    (2006.01)
*G01N 23/00*    (2006.01)
(Continued)

(52) U.S. Cl.
CPC .............. *A61L 2/087* (2013.01); *A61L 2202/11* (2013.01); *A61L 2202/23* (2013.01); *H01J 2237/31* (2013.01)
USPC .............. 422/22; 422/1; 422/24; 422/186.04; 250/455.11; 250/492.1; 250/492.3

(58) Field of Classification Search
CPC .............. A61L 2/00; A61L 9/03; A61L 9/18; A61L 9/20

USPC ................ 422/1, 22, 24, 186.04; 250/455.11, 250/492.1, 492.3
See application file for complete search history.

(56) References Cited

U.S. PATENT DOCUMENTS

| | | | |
|---|---|---|---|
| 6,139,796 A | 10/2000 | Kristiansson et al. | .......... 422/22 |
| 6,221,216 B1 | 4/2001 | Nablo et al. | ............. 204/157.15 |
| RE39,657 E | 5/2007 | Wakalopulos et al. | .... 250/492.3 |

(Continued)

FOREIGN PATENT DOCUMENTS

| | | |
|---|---|---|
| CN | 101310773 | 11/2008 |
| CN | 101557832 | 10/2009 |

(Continued)

OTHER PUBLICATIONS

German Search Report issued for 10 2011 055 005.4, dated Sep. 12, 2012 (5 pgs).

(Continued)

*Primary Examiner* — Monzer R Chorbaji
(74) *Attorney, Agent, or Firm* — Hayes Soloway P.C.

(57) ABSTRACT

An apparatus for sterilization of an inner wall of containers has a charge carrier source for generating charge carriers, with an acceleration device by which charge carriers are capable of being accelerated in the direction of a charge carrier emission window. The charge carrier emission window is arranged on a treatment device for introduction through an opening into the container along an insertion direction, in order to act upon an inner wall of the container with the charge carriers issuing from the charge carrier emission window. A medium is flowed into the region of the charge carriers issuing out of the charge carrier emission window for changing the dimension of a charge carrier cloud formed by the discharged charge carriers.

14 Claims, 3 Drawing Sheets

(51) Int. Cl.
*A61N 5/00* (2006.01)
*A61L 2/08* (2006.01)

(56) References Cited

U.S. PATENT DOCUMENTS

| | | | |
|---|---|---|---|
| 8,294,126 B2 | 10/2012 | Humele et al. | 250/492.3 |
| 2008/0138243 A1 | 6/2008 | Kristiansson et al. | 422/23 |
| 2009/0045350 A1* | 2/2009 | Humele et al. | 250/455.11 |
| 2010/0054987 A1 | 3/2010 | Krueger et al. | 422/3 |
| 2011/0076187 A1 | 3/2011 | Foell et al. | 422/22 |

FOREIGN PATENT DOCUMENTS

| | | |
|---|---|---|
| DE | 19882252 | 5/2000 |
| DE | 102008025868 | 12/2009 |
| EP | 1982920 | 10/2008 |
| EP | 2103528 | 9/2009 |
| EP | 2161202 | 3/2010 |
| EP | 2246265 | 11/2010 |
| WO | WO9707024 | 2/1997 |
| WO | WO02058742 | 8/2002 |
| WO | WO2008073015 | 6/2008 |

OTHER PUBLICATIONS

Chinese Office Action (with translation) issued in related application No. 201210432382.6, dated Jun. 27, 2014 (14 pgs).
European Search Report (no translation) issued in related application No. 12191094.7, dated Mar. 25, 2013 (7 pgs).

* cited by examiner

APPARATUS FOR THE STERILIZATION OF PLASTICS MATERIAL CONTAINERS BY MEANS OF MEDIUM-CONTROLLED ELECTRON BEAMS

BACKGROUND OF THE INVENTION

The invention relates to an apparatus for the sterilization of containers and, in particular, an inner wall of containers by means of accelerated charge carriers with a charge carrier source for producing the charge carriers, with an acceleration device by which charge carriers are capable of being accelerated in the direction of a charge carrier emission window, the charge carrier emission window being arranged on a treatment device which is capable of being introduced through an opening into the container along an insertion direction, in order to act upon an inner wall of the container with the charge carriers issuing from the charge carrier emission window, the treatment device having a medium line with a medium emission opening, the medium emission opening of which is preferably capable of being introduced through the opening into the container.

The invention further relates to a plant for the treatment of containers, which has at least one apparatus for sterilizing containers, as well as to a method of sterilizing containers and, in particular, an inner wall of containers by means of accelerated charge carriers, the charge carriers being generated in a charge carrier source and being accelerated by an acceleration device in the direction of a charge carrier emission window, the charge carrier emission window being arranged on a treatment device which is introduced through an opening into the container along an insertion direction, in order to act upon an inner wall of the container with the charge carriers issuing from the charge carrier emission window, the treatment device having a medium line with a medium emission opening, the medium emission opening of which is capable of being introduced through the opening into the container.

As well as the actual filling procedure, the sterilization of a container to be filled is the central process step in an aseptic filling plant. The possible forms of sterilization vary with respect to the disinfectants and the performance of the process. What they all have in common, however, is that the destroying action is carried out on the basis of chemical processes. In this way, it is known for example for the inner wall of containers to be sterilized with steam or hydrogen peroxide. Methods of this type, however, are subject to drawbacks since the treatment with hydrogen peroxide for example can result in a softening of the material. Recent developments differ from this and use ionizing radiation in order to achieve a reduction in germs. In most applications this radiation comprises accelerated electrons which are produced in a suitable plant and are introduced into the container to be sterilized. This results in a reduction or complete avoidance of the use of chemical substances and inter alia a reduction in the costs of acquisition and disposal.

The terms "container", "receptacle" and "plastics material container" are used synonymously below for the sake of simplification. In this case these terms also include preliminary products of containers of this type. In particular, these terms relate to bottles, preferably drinks bottles, but also to pre-forms (plastics material pre-forms for example for bottles for example).

Suitable systems for sterilization known from the prior art comprise an electron production apparatus and a bundling device. Charge carriers produced outside the container to be sterilized are directed by various elements, for example mechanical or electronic elements, into the container to be sterilized. In the latter a cloud of electrons is formed which deactivates any undesired micro-organisms by interaction with the latter.

In this way, DE 198 82 252 T1 describes a technique for the internal sterilization of a container by means of electrons. In this case an electron beam source is likewise provided which directs the radiation into the interior of the container from the outside.

Methods are also known, such as for example from the publication WO 97/07024 A, in which at least parts of the electron source can be introduced into the interior of the container. A method of cleaning and sterilizing packages of products by means of a combination of an electron beam and a gas jet is described. The apparatus disclosed in WO 97/07024 A comprises an electron gun which is capable of being introduced in part into the interior of a container and which introduces accelerated electrons into the interior of a container. A flow—introduced parallel thereto—of a gas interacting with the electron beam is used either for deflecting the electron beam in the direction of the gas flow or, on the other hand, as an auxiliary agent for sterilization by ionization of the gas.

In many cases, however, it is also desirable for the geometry of the electron cloud to be changed, and in particular for the extension thereof to be reduced. An advantage of a process with a controlled reduction of the electron cloud consists in the possibility of the radiator power and thus also the dimension of the resulting cloud being adapted to containers which are reduced for example, such as for example container pre-forms, without changing the radiator setting, for example the acceleration voltage. Excessively accelerated electrons could penetrate too deeply into the material of the pre-form, without being able to interact to an adequate degree with the surface and contamination present on the latter and thus being able to sterilize the surface. In addition, excessively accelerated charge carriers could possibly—depending upon the material of the container used—also damage the material of the container.

It would be particularly advantageous if the extension of the electron cloud could be reduced into one region in which the radiation which is issuing from the treatment device and which can include both the charge carrier beam and also interfering radiation, for example x-ray radiation, can be substantially screened off from the environment and, in this way, in the event of a removal of the treatment device from the container to be sterilized, an unnecessary exposure of the environment to radiation can be avoided. This could be advantageous for example in the case of a change of the containers to be sterilized, in which the treatment device and thus also the electron cloud discharged are outside a container for a brief time.

The object of the invention is therefore to provide an apparatus for the sterilization of containers, which will make it possible, without switching off or changing the acceleration voltage, to change, and in particular to reduce, the dimension of an electron cloud radiated by a treatment device.

Since, in particular, high clock-time rates and throughput figures are achieved in the plants used for the production and filling of containers, it is in addition an object of the invention to provide a suitable plant for the treatment of containers, which includes an apparatus of this type for the sterilization of containers.

In addition, it is an object of the invention to provide a method of sterilizing containers, which will make it possible, without switching off or changing the acceleration voltage, to change and, in particular, to reduce the dimension of an electron cloud radiated by a treatment device.

SUMMARY OF THE INVENTION

An essential aspect of the invention is an apparatus for the sterilization of containers and, in particular, an inner wall of containers by means of accelerated charge carriers with a charge carrier source for producing the charge carriers, with an acceleration device by which charge carriers are capable of being accelerated in the direction of a charge carrier emission window, the charge carrier emission window being arranged on a treatment device which is capable of being introduced through an opening into the container along an insertion direction, in order to act upon an inner wall of the container with the charge carriers issuing from the charge carrier emission window, the treatment device having a medium line with a medium emission opening, the medium emission opening of which is preferably capable of being introduced through the opening into the container, the treatment device having at least one projection which protrudes with respect to the charge carrier emission window in the insertion direction and which is suitable for absorbing interfering radiation, and the medium line being capable of having a medium flow through it which is capable of being discharged through the medium emission opening at least into the region of the charge carriers issuing out of the charge carrier emission window, the medium being suitable for changing the dimension of a charge carrier cloud formed by the issuing charge carriers.

With an apparatus of this type it is possible to reduce or to enlarge the dimension of the charge carrier cloud formed by the issuing charge carriers without changing the parameters which influence the occurrence and acceleration of the charge carriers before the charge carriers pass through the charge carrier emission window. In particular, irrespectively of the power of the radiator, it is possible to influence the geometry of the electron cloud, which represents a key criterion of the success of the sterilization. The advantage of a process control of this type lies in the ability to adapt the charge carrier cloud which occurs to containers which are reduced for example, such as for example pre-forms, without changing the radiator setting. By way of example, it is possible by means of an apparatus of this type to retain a set radiator power, even if the sterilization process is changed over and a change is carried out from a large container with a volume of for example 1.5 l to a smaller container such as for example a pre-form with a correspondingly smaller volume and smaller surface. For a pre-form of this type the acceleration of the charge carriers suitable for the sterilization of the 1.5 l container would be too strong without subsequent modulation and the charge carriers would thus penetrate too deeply into the material of the pre-form itself, without adequately sterilizing the surface, or even damage the material of the pre-form permanently.

The cross-section of the treatment device is structured in such a way that the treatment device is capable of being guided at least in part, preferably with the treatment head, through the aperture of the container.

The acceleration device accelerates the charge carriers in such a way that the charge carriers issuing out of the emission window are preferably capable of being directed directly onto an inner wall of the container.

The charge carriers are, in particular, electrons, but it would also be possible for other charge carriers, such as ions, to be used.

It is particularly preferred for the charge carrier emission window to be produced from a material which is selected from a group of materials which contains titanium, quartz glass, diamond, combinations thereof and the like.

In the case of the apparatus according to the invention it is possible for the medium line to have a medium conveyed through it which influences the charge carriers after they have passed through the charge carrier emission window. In particular, it is possible to brake charge carriers and/or to reduce them in their (acceleration) energy or their impetus. This can be carried out for example by the introduction of a heavy gas or another medium and so the desired effect on the inner wall of the pre-form can be achieved. In this respect, a heavy gas is understood to be, in particular, gases of a large effective cross-section, a large impact cross-section, a high density and/or a strong interaction with charge carriers. Media which have a large effective cross-section or impact cross-section in the case of the kinetic energy of the charge carriers are particularly advantageous.

It is likewise possible for the opposite case to be implemented. In this way, when changing the containers a comparative pre-set acceleration voltage and thus for example the kinetic energy of the charge carriers can be too small for an adequate sterilization of the surface (for example the inner surface) of the containers. This can occur for example when changing from a small container to a larger container (of larger receptacles). By introducing a suitable medium, for example light gas, the reach of the sterilizing charge carriers (for example electrons) can be increased in the case of a given acceleration voltage. A light gas is understood below to be, in particular, gases of a small effective cross-section, of a small impact cross-section, a low density and/or a weak interaction with gas molecules. As a result of the introduction of a medium of this type a medium possibly present in the region of the charge carrier cloud and having a larger effective cross-section, a larger impact cross-section, a higher density and/or a stronger interaction with charge carriers can be displaced and the reach of the charge carriers can be increased.

A further possibility of influencing the dimension of the charge carrier cloud consists in increasing or reducing the pressure in the chamber, e.g. the gas pressure. In this case, in particular, a change in the pressure, preferably the gas pressure in the region of the charge carrier cloud is advantageous. The manner of operation corresponds to that of the described methods of varying the density.

A further essential aspect of the invention with respect to the apparatus for the sterilization of containers is that the treatment device has at least one projection which protrudes with respect to the charge carrier emission window in the insertion direction and which is suitable for absorbing interfering radiation. This projection is preferably arranged in the vicinity of the charge carrier emission window and extends from a plane formed by the charge carrier emission window at least also in the direction of the issuing charge carrier beam and has a (vector) component in this direction. It is preferable for the projection to be arranged perpendicularly to the plane formed by the charge carrier emission window. Designs are also possible, however, in which the projection deviates from the perpendicular by an angle of up to $\pm 10°$, $\pm 20°$, $\pm 30°$ or even up to $\pm 45°$.

In particular, angles of the projection are preferred in which the end of the projection remote from the charge carrier emission window is inclined in the direction of a central longitudinal axis of the treatment device, preferably an axis extending through the centre of the charge carrier emission window, so that interfering radiation striking the projection is preferably reflected in the direction of the charge carrier emission window.

This also affords, in addition, advantages in the case of the introduction into the container, since this results in a frustoconical shape of the tip of the treatment device which—even if a central axis of the container or the opening thereof should be arranged slightly offset with respect to a central axis of the treatment device—is still capable of being introduced into the container without damage to the container or the tip of the treatment device.

The projection is used to absorb interfering radiation and/or electrons. Interfering radiation occurs in particular in the vicinity of the charge carrier production, for example in the form of x-ray radiation. Other types of interfering radiation, however, are also possible. In particular, interfering radiation can also have charge carriers, for example scattered electrons. Interfering radiation is disadvantageous in particular in the region of the charge carrier emission window, since at least the head of the treatment device on which the charge carrier emission window is arranged is usually introduced through an opening into the container. The opening in the container is usually one of the narrowest places of the container, so that the treatment device and also the charge carrier emission window come very close to the wall of the container. Interfering radiation can therefore reach the wall in this region with very high energy and, as described above, can lead to inadequate sterilization of this region or even to damage of the material of the container.

The portion of the interfering radiation occurring outside the treatment device is distributed over a region of which the size also depends upon the size of the charge carrier cloud. In the case of a relatively large charge carrier cloud the region in which interfering radiation is discharged is greater than in the case of a relatively small charge carrier cloud. In the case of a fixed size, in particular in the case of a fixed length of the projection and in the case of a large charge carrier cloud, therefore, it happens to an increased degree that interfering radiation does not strike the projection but can pass it without obstruction.

In order to reduce this effect, in a preferred embodiment of the apparatus for the sterilization of containers the medium capable of being discharged into the region of the charge carriers issuing out of the charge carrier emission window is suitable for reducing the dimension of a charge carrier cloud formed by the issuing charge carriers, in such a way that interfering radiation is capable of being conveyed up to at least 25%, preferably at least 50%, preferably at least 60%, preferably at least 70%, preferably at least 80%, and in a particularly preferred manner at least 90%, to the projection protruding with respect to the charge carrier emission window and is capable of being absorbed by the aforesaid projection.

An enlargement of the charge carrier cloud, however, would also be possible.

As a result it is possible for the dimension of the charge carrier cloud to be reduced at least temporarily to the degree that at least the portion of the interfering radiation occurring outside the treatment device can strike the projection in larger portions and can be absorbed by the latter.

The possibility of varying the geometry of an electron cloud can also serve to improve the safety engineering. If certain critical method parameters are present, the introduction of suitable medium, for example gas for producing a greater density, can be used for the sudden decrease (reduction of the dimension) of the electron cloud in a manner dependent upon the detection and reaction speed of the apparatus described. Although the production of x-ray radiation is influenced by this to only a minimal degree, the place of production (for interfering radiation, in particular for x-ray radiation) is shifted closer to the radiator or the treatment device, in an ideal case very close to the actual emission window. The place of occurrence of interfering radiation is thus set in the vicinity of the metallic finger, so that with a suitable design of the finger a first deflection is achieved. As a consequence of this the screening additionally present has to screen off less interfering radiation. A portion of the interfering radiation can already be absorbed, converted, deflected or otherwise rendered harmless close to the place of occurrence by the projection.

An embodiment of the apparatus for the sterilization of containers is preferred in which the medium line is capable of having a medium flow through it which is suitable for changing at least one physical property, preferably the density, of a further medium, preferably a gas, arranged in the region of the charge carrier cloud formed by the issuing charge carriers. As already mentioned, the choice of the media is not restricted only to media which change the density of the medium arranged in the region of the charge carrier cloud formed by the issuing charge carriers, but also includes media which change other physical properties, preferably its effective cross-section, its impact cross-section and/or its interaction with charge carriers.

An embodiment of the apparatus for the sterilization of containers is particularly preferred in which the medium line has a curved shape at least locally, the medium line preferably being designed in such a way that the medium capable of being conveyed in it is capable of being discharged through the medium emission opening in the direction of the charge carrier cloud (i.e. with a (vector) component in this direction), in a particularly preferred manner in a direction substantially opposed to an acceleration direction of the charge carriers. It is preferable for at least one portion of the medium line to be curved in this case and preferably curved by an angle which is greater than 60°, preferably greater than 90°, preferably greater than 120°, preferably greater than 150°.

It would also be possible, however, for deflecting devices for deflecting the medium to be provided, which could be arranged for example at the medium emission opening.

On account of this embodiment the medium flows in a direction substantially opposed to the accelerated charge carriers. This has the advantage on the one hand that, on account of the mass flow and the interaction resulting therefrom with the mass flow of the charge carriers, the latter are already deflected, and in particular braked, to a slight degree. Even more influential in this context, however, is the fact that on account of this embodiment it is possible to ensure that medium flows continuously in the direction of the charge carrier emission window and other media in the region upstream of the emission window are thus continuously attenuated or even almost completely moved out of this region. In this embodiment the medium flowing in the direction of the charge carrier emission window ensures that the concentration of the medium is very high in the region of the charge carrier emission window and charge carriers are already braked by interaction with the medium immediately after passing through the charge carrier emission window. The formation of reservoirs, in which the medium previously present is not replaced by the new medium discharged out of the medium emission opening, is prevented in the region of the charge carrier emission window. In the event of a discharge of the medium in a direction extending substantially parallel to the emission direction of the charge carriers out of the treatment device, it would be conceivable for residues of the medium previously present to remain in particular in regions which are situated in the flow shadow of the projection.

In a particularly preferred embodiment of the apparatus for sterilizing containers the projection protruding with respect to the charge carrier emission window extends at least locally along a periphery of the treatment device, preferably around the complete periphery, in a particularly preferred manner in the form of a circular cylinder (in particular straight).

The projection can be designed in the form of an individual element or it can also comprise a plurality of elements. The projection is preferably arranged in such a way that it is situated between a place of origin for interfering radiation and a region to be protected, in particular, from this radiation. In the event that for example a narrow neck of a container is to be protected from the interfering radiation, it is advantageous if the projection also surrounds the place of origin for interfering radiation along a complete periphery. In this way, the neck of the container, which surrounds the treatment device or a head of the treatment device on the entire periphery, can be screened off uniformly from interfering radiation.

The mentioned variant of embodiment of the projection in the form of a straight circular cylinder is preferred, since with a small requirement of material a particularly large region can be protected from interfering radiation in this way. As already mentioned, however, designs of the projection are also possible in which the projection deviates from the perpendicular by an angle of up to ±10°, ±20°, ±30° or even up to ±45°. In this case, in particular, angles are preferred in which the end of the projection remote from the charge carrier emission window is inclined in the direction of the longitudinal axis of the treatment device extending through the centre of the charge carrier emission window. In the case of a design of the projection over the entire periphery the projection thus is in the shape of the frustum of a cone. As a result, it is made possible for interfering radiation striking the projection to be reflected preferably in the direction of the charge carrier emission window, where it can be kept by other screening devices integrated in the treatment device from passing in an uncontrolled manner into the environment. In this way, it is possible for an uncontrolled radiation to be sharply reduced.

It is also possible for the projection to be produced in a multiple-layer variant. In this variant a side of the projection facing the charge carrier cloud is produced essentially from a screening material which essentially has atoms of a low atomic number. In the absorption of some types of charge carriers, for example electrons, atoms of a low atomic number have the advantage that only a low proportion of the kinetic energy of the charge carriers is converted into braking radiation, in particular into x-ray radiation. It is preferable for a metallic layer to be involved, preferably of a light metal, for example aluminium. Non-metallic materials, such as for example plastics materials, however, are also possible.

A further layer, which in particular is suitable for screening the environment from x-ray radiation, is arranged inside the projection radially outside this layer of screening material consisting of atoms of a low atomic number. This layer essentially consists of at least one metal of a high atomic number (heavy metal), these absorb x-ray radiation particularly well. In this way, the environment can also be protected from the x-ray radiation occurring as braking radiation in the layer of the projection facing the charge carrier cloud.

In a preferred embodiment of the apparatus for the sterilization of containers the medium line is connected at least locally to the treatment device, is preferably integrated in the latter and is movable jointly with the treatment device. A major advantage of this embodiment is that a common device can be used for introducing the treatment device and the medium line into the container. In particular, however, this places demands upon the dimensioning of the treatment device, since the latter has to have a particularly small cross-section.

It is possible in this case for the medium line to be arranged at the side of the treatment device. In this case the medium line preferably extends radially outside the projection.

It is also possible for a plurality of medium lines to be arranged at the side of the treatment device. This is particularly advantageous if a highly homogeneous discharge of the medium is required. By way of example, this can be necessary if a symmetrical shape of the charge carrier cloud is required and the charge carriers are pressed by feeding the medium to the side of the treatment device opposite the medium emission opening with respect to a longitudinal axis of the treatment device.

In addition, it is provided in one embodiment that the medium line is integrated at least locally in the treatment device. In the case of this embodiment the medium line preferably extends radially inside the projection. This embodiment permits a particularly simple supply of the medium into the region present radially inside a projection extending along a periphery of the treatment device over the entire periphery, i.e. the region which is arranged upstream of the charge carrier emission window directly in the radiation direction of the charge carriers. As a result, it is possible for residues of the medium previously present in this region to be prevented particularly effectively from remaining. It is preferable for a medium line and/or a medium emission opening to be provided in a region which is situated between the projection and the charge carrier emission window. In the case of an annular charge carrier emission window it is possible for a medium line and/or a medium emission opening to be arranged in the centre of the charge carrier emission window.

It is preferable for the medium line to extend at least locally parallel to an outer wall of the treatment device. It is particularly preferable for the medium line to extend at least locally parallel to the longitudinal axis of the projection.

It is preferable for the treatment device to have an outer casing which has the charge carrier emission window. In order to cool the charge carrier emission window it is preferably provided that an inner casing is arranged inside the outer casing and at a distance from it, so that a region in which a cooling medium is capable of being conveyed is formed between the inner casing and the outer casing. It is preferable for this region to be divided into various divisions in which different media can be conveyed and/or in which the medium flows in different directions. In this way, for example, a defined supply and outflow of the cooling medium to the charge carrier emission window and away from it can be set.

In addition, a plant for the treatment of containers forms the subject matter of the present invention, which has at least one apparatus, preferably a plurality of apparatus for the sterilization of containers and in particular an inner wall of containers by means of accelerated charge carriers with a charge carrier source for producing the charge carriers, with an acceleration device by which charge carriers are capable of being accelerated in the direction of a charge carrier emission window, the charge carrier emission window being arranged on a treatment device which is capable of being introduced through an opening into the container along an insertion direction, in order to act upon an inner wall of the container with the charge carriers issuing from the charge carrier emission window, the treatment device having a medium line with a medium emission opening, the medium emission opening of which is preferably capable of being introduced through the opening into the container, the treatment device having at least one projection which protrudes with respect to the charge carrier emission window in the insertion direction and which is suitable for absorbing interference radiation, and the medium line being capable of having a medium flow through it which is capable of being discharged through the medium emission opening at least into the region of the charge carriers issuing out of the charge carrier emission window, the medium being suitable for changing the dimension of a charge carrier cloud formed by the issuing charge carriers.

By means of a plant of this type it is possible to carry out a sterilization of containers, in particular at the high clock-time rates and throughput rates used in the production and filling of containers.

It is preferable for a plant of this type to have a further apparatus for sterilization, preferably for the sterilization of an outer wall of the containers.

In a further preferred embodiment the plant has an insertion device by means of which the treatment device is capable of being introduced into the interior of a container, the container and the treatment device being movable relative with respect to each other (in particular in a longitudinal direction of the container), it being possible for the relative mobility to be implemented by movement of the treatment device in the direction of the container, by movement of the container in the direction of the treatment device and/or by a combination of the two movements.

Depending upon the embodiment of the plant it may be advantageous for the treatment device to be moved in the direction of the container, in order to introduce it into the latter for the sterilization thereof. In the case of a particularly complicated apparatus for the production and acceleration of the charge carriers, however, the precise control of the treatment device is possibly very complicated, so that a movement of the container in the direction of the treatment device is advantageous. In some embodiments a combination of the two movements mentioned above can also be advantageous, for example in order to permit a particularly rapid insertion of the treatment device into the container.

It is preferable for the plant to have a conveying device which moves the containers along a pre-set conveying path, in particular also during the sterilization thereof. It is advantageous for the conveying device to be a rotatable carrier on which it is particularly preferred for a plurality of gripping elements to be arranged.

It is preferable for the plant to have a device for filling containers and for the apparatus according to the invention to be arranged upstream with respect to this device.

It is preferable for the plant to have a further apparatus for the sterilization of an outer wall of the containers.

In addition, it is preferred for the plant to have at least one conveying element, preferably a conveying star wheel, which is suitable for taking a container from an apparatus for the sterilization of containers and for transferring it to a further apparatus for sterilization.

A further essential aspect of the invention is a method of sterilizing containers, and in particular an inner wall of containers by means of accelerated charge carriers, the charge carriers being produced in a charge carrier source and being accelerated with an acceleration device in the direction of a charge carrier emission window, the charge carrier emission window being arranged on a treatment device which is introduced through an opening into the container along an insertion direction, in order to act upon an inner wall of the container with the charge carriers issuing from the charge carrier emission window, the treatment device having a medium line with a medium emission opening, the medium emission opening of which is capable of being introduced through the opening into the container, the treatment device having at least one projection which protrudes with respect to the charge carrier emission window in the insertion direction and which can absorb radiation, and the medium line being capable of having a medium flow through it which is capable of being discharged through the medium emission opening at least into the region of the charge carriers issuing out of the charge carrier emission window, the medium changing the dimension of a charge carrier cloud formed by the issuing charge carriers.

By means of this method it is thus possible to exert influence upon the geometry of the electron cloud and to change the dimension thereof. To this end, media, for example fluids, in particular gases and preferably substances heavier or lighter than air in this case, are introduced into the radiation chamber, in particular into the region of the charge carrier cloud. As an alternative or in addition, the pressure in the chamber, preferably in the region of the charge carrier cloud, can also be increased or reduced by the supply or removal of air. On account of these measures the density in the process chamber and in particular in the region of the charge carrier cloud is increased or reduced and so a virtually immediate reduction in the dimensions of the charge carrier cloud, for example an electron cloud, is made possible. The possibility of varying the pressure allows the sterilization process to be suddenly interrupted by blowing air or another medium in a purposeful manner into the container. This results in special possibilities of increasing the (existing) safety engineering.

A variant of the method of sterilizing containers and, in particular, an inner wall of containers by means of accelerated charge carriers is preferred in which the medium discharged into the region of the charge carriers issuing out of the charge carrier emission window reduces the dimension of a charge carrier cloud formed by the issuing charge carriers, in such a way that interfering radiation is conveyed up to at least 25%, preferably at least 50%, preferably at least 60%, preferably at least 70%, preferably at least 80%, and in a particularly preferred manner at least 90%, to the projection protruding with respect to the charge carrier emission window and is capable of being absorbed by the aforesaid projection.

This method variant makes it possible to reduce an electron cloud required for the sterilization of a large container to the extent that even a substantially smaller container can be sterilized on the inner surface thereof with the radiation intensity optimum for this container. In particular, in the case of changing the sterilization between pre-forms and drinks bottles, it is necessary to change the dimension of the charge carrier cloud by a large factor.

In addition, a variant of the method of sterilizing containers and, in particular, an inner wall of containers by means of accelerated charge carriers is preferred in which, in the case of a reduction in the dimension of the charge carrier cloud formed by the issuing charge carriers by the medium, the intensity of the interfering radiation is reduced by the projection protruding with respect to the charge carrier emission window to a degree at which when changing the container to be sterilized it becomes superfluous to interrupt the acceleration of the charge carriers from the charge carrier source with the acceleration device in the direction of the charge carrier emission window.

By means of this method variant it is possible for the charge carrier cloud to be reduced to the degree that interfering radiation occurs in a high proportion in the region which is situated upstream of the charge carrier emission window and adjacent to the projection protruding with respect to the charge carrier emission window. In this region it is possible in a particularly satisfactory manner to absorb interfering radiation by the projection or to convert it into other types of radiation. Accordingly, the radiation discharged in an uncontrolled manner by the treatment device can also therefore be substantially reduced outside a container. As a result, it is possible for the treatment device to be removed from the container without switching off or reducing the production of charge carriers or the acceleration thereof by means of the acceleration device. As a result, it is possible to dispense with corresponding control devices and for the treatment device to be designed in a particularly simple and compact manner. This can be advantageous with respect to manufacturing and acquisition costs and simplifies the possibility of movement of the treatment device.

BRIEF DESCRIPTION OF THE DRAWINGS

Further advantages and embodiments are evident from the accompanying drawings. In the drawings

DETAILED DESCRIPTION OF THE INVENTION

Figure 1:
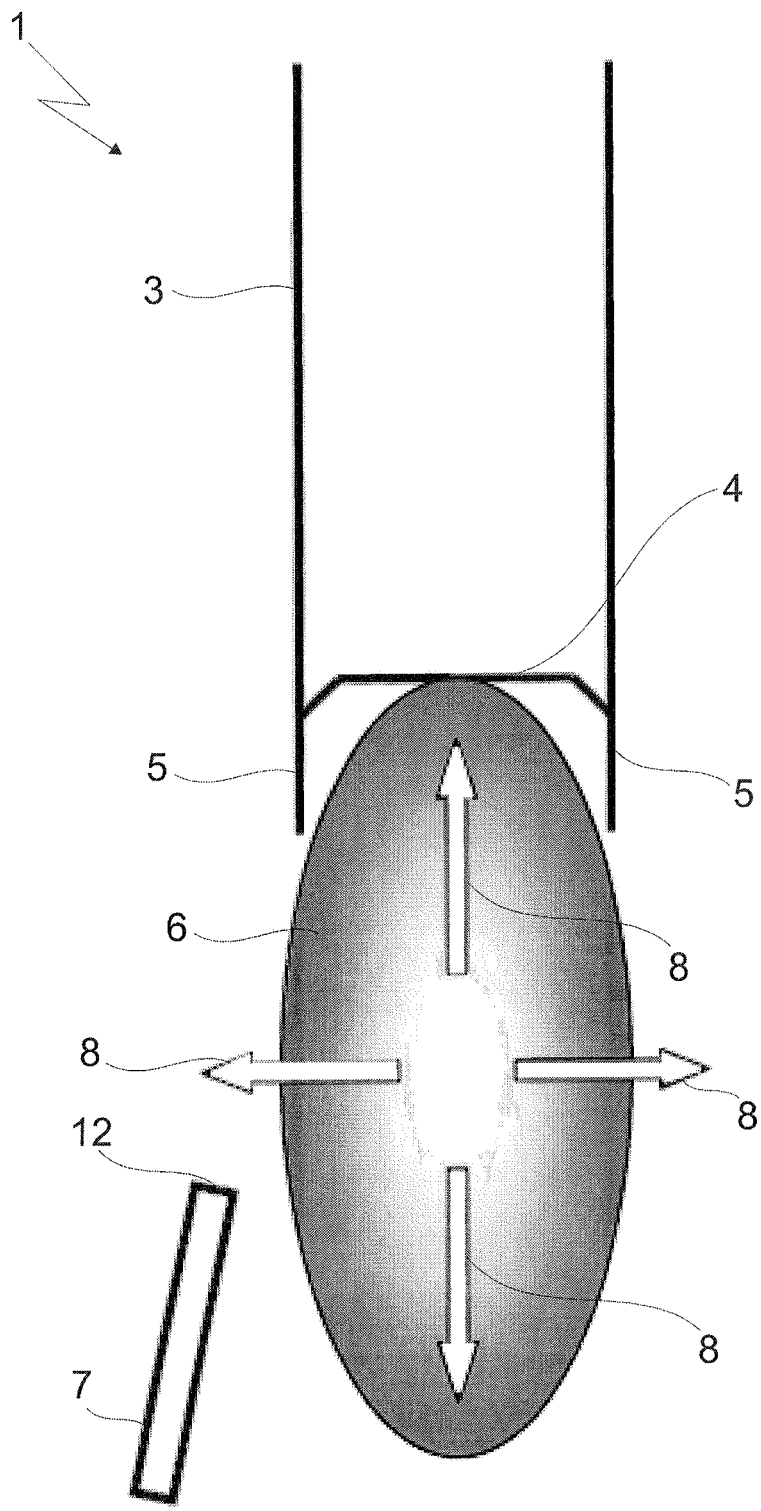
FIG. 1 is a diagrammatic illustration of a side view of a treatment device with a projection protruding with respect to the charge carrier emission window for the sterilization of containers by means of accelerated charge carriers without the supply of the medium for changing the dimension of a charge carrier cloud formed by the issuing charge carriers.

FIG. 1 is a diagrammatic illustration of a side view of a treatment device 1. The latter has a projection 5 protruding with respect to the charge carrier emission window 4. The apparatus for the sterilization of containers 2 by means of accelerated charge carriers is illustrated in this case without the supply of the medium 9 for changing the dimension of a charge carrier cloud 6 formed by the issuing charge carriers. Of the treatment device 1 there is shown a radiation finger 3 which is capable of being introduced at least locally into a container 2 and from which the charge carriers issue. The charge carrier source for the production of the charge carriers and the acceleration device, by which charge carriers are capable of being accelerated in the direction R of a charge carrier emission window 4, are not shown. The charge carrier emission window 4 is situated in a wall of the radiation finger 3 which is capable of being introduced into a container 2. The charge carrier emission window 4 is situated in a beam path of the charge carriers and allows the passage of the charge carriers out of the interior of the radiation finger 3 into the environment.

In addition, a medium line 7 with a medium emission opening 12 is shown.

A charge carrier cloud 6 with a defined extension, which can sterilize a container 2, is formed on the outside of the charge carrier emission window 4 in a manner dependent upon the charge carriers produced and the kinetic energy transmitted by means of the acceleration device to the charge carriers.

A projection 5, which extends beyond the casing 3 of the radiation finger in the radiation direction of the charge carriers, is arranged at the side of the charge carrier emission window 4. In the example shown, this is a continuous projection 5 in the form of a straight circular cylinder, the external radius of which corresponds to that of the radiation finger 3. This has the advantage that no irregularities occur on the outside at the transition between the casing of the radiation finger 3 and the projection 5 and so it is possible to prevent becoming caught during the insertion or withdrawal into or out of a container 2.

In the example shown the projection 5 has a length which corresponds approximately to the radius of the casing of the radiation finger 3. Lengths of the projection 5 which deviate significantly from the latter are also, however, possible. It is preferable for the length of the projection 5 to amount to at least 1/10, preferably 1/5, and in a particularly preferred manner 1/3, of the radius of the casing of the radiation finger. A maximum length of the projection 5 is not defined, but lengths of less than half a length of the container 2 to be sterilized, preferably less than 10 times the length of the radius of the casing of the radiation finger, preferably less than 5 times the length of the radius of the casing of the radiation finger, and in a particularly preferred manner less than 3 times the length of the radius of the casing of the radiation finger have been found to be advantageous.

The projection 5 can thus absorb or screen off interfering radiation 8, in this case in particular scattered radiation, which occurs as a result of reflection and scattering in the interior of the radiation finger 3 and by interaction with the charge carrier emission window 4.

Interfering radiation 8, which is formed from the charge carrier cloud 6 outside the region bounded by the projection 5, is symbolized diagrammatically by the arrows 8. Depending upon the direction of the interfering radiation 8, the latter can radiate onto the treatment device 1 or can also be radiated into the environment.

Figure 2:
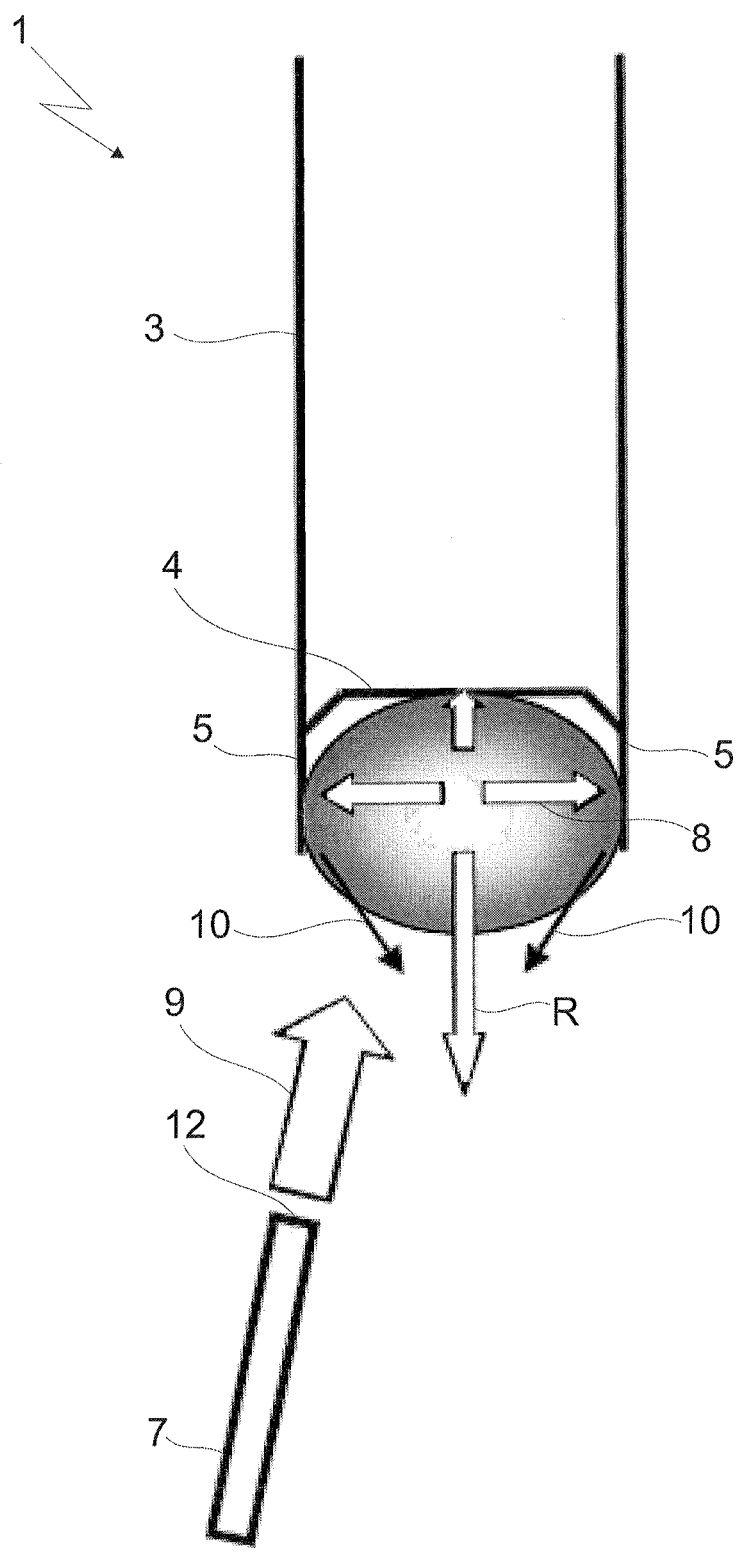
FIG. 2 is a diagrammatic illustration of a side view of a treatment device with a projection protruding with respect to the charge carrier emission window for the sterilization of containers by means of accelerated charge carriers during the supply of the medium for changing the dimension of a charge carrier cloud formed by the issuing charge carriers.

FIG. 2 is a diagrammatic illustration of a side view of a treatment device 1 with a projection 5 protruding with respect to the charge carrier emission window 4 for the sterilization of containers 2 by means of accelerated charge carriers during the supply of the medium 9 for changing the dimension of a charge carrier cloud 6 formed by the issuing charge carriers.

The situation illustrated in FIG. 2 differs from that illustrated in FIG. 1 essentially in that a medium 9 is conveyed out of the medium line 7 with a medium emission opening 12 into the region outside the treatment device 1. This medium 9 causes a change in the reach of the charge carriers issuing through the charge carrier emission window 4 and thus reduces the size of the charge carrier cloud 6 in the case illustrated.

As a result, the charge carrier cloud 6 formed outside the radiation finger 3 is also significantly reduced and interfering radiation 8 formed from it and symbolized diagrammatically by the arrows 8 is radiated in a greater portion in a region from which it strikes the projection 5. When striking the projection 5 this radiation can be absorbed or converted, so that the portion of radiation discharged into the environment in an uncontrolled manner is significantly reduced.

The thinner arrows 10 symbolize residual radiation 10, which has not been absorbed or converted but reflected by the projection 5. The portion thereof can be reduced in accordance with requirements depending upon the nature of the charge carriers, the materials used in the projection 5 and the geometry of the projection 5.

Figure 3:
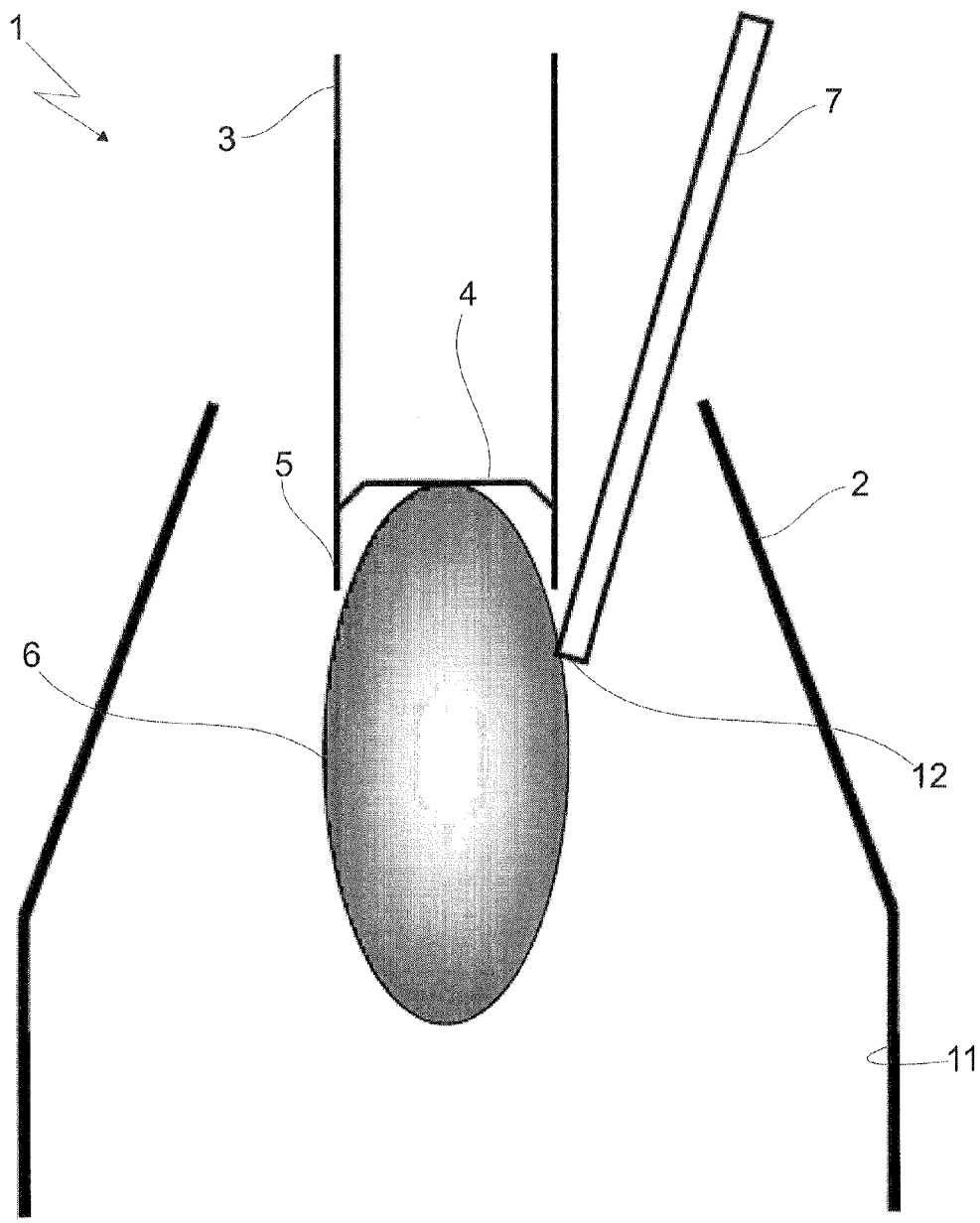
FIG. 3 is a diagrammatic illustration of a side view of a treatment device with a projection protruding with respect to the charge carrier emission window for the sterilization of containers by means of accelerated charge carriers, which is introduced into a container.

FIG. 3 is a diagrammatic illustration of a side view of a treatment device 1 with a projection 5 protruding with respect to the charge carrier emission window 4 for the sterilization of containers 2 by means of accelerated charge carriers, which is introduced into a container 2.

Of the treatment device 1 only the radiation finger 3 with the projection 5 capable of being introduced into the container 2 is also shown in this figure. The charge carrier cloud 6 is likewise evident which issues out of the radiation finger 3 into the container 2 through the charge carrier emission window 4. The charge carrier source for the production of the charge carriers and the acceleration device, by which charge carriers are capable of being accelerated in the direction of an emission window, are not shown. The medium line 7 with a medium emission opening 12, which is likewise introduced into the container 2 at least locally, is shown at the side of the radiation finger 3.

The medium emission opening 12 is situated in the vicinity of the charge carrier cloud 6, so that issuing medium 9 can immediately influence it.

In contrast to the embodiments shown in FIGS. 1 and 2, in the example shown in FIG. 3 the medium line 7 extends as far as the medium emission opening 12 substantially parallel to the charge carrier radiation device. This embodiment is less preferred since in this way the exchange of the medium 9 is delayed in the region which, protected by the projection 5, is situated immediately upstream of the charge carrier emission window 4.

If, however, the change in the dimension of the charge carrier cloud 6 is to be used for adaptation to the size of the container, the embodiment shown is advantageous, since a rapid exchange of the medium can take place in this way in the container 2 with a low outlay in terms of the apparatus. The straight design of the medium line 7 permits particularly rapid flows of the medium.

The Applicants reserve the right to claim all the features disclosed in the application documents as being essential to the invention, insofar as they are novel either individually or in combination as compared with the prior art.

LIST OF REFERENCES 1 apparatus for the sterilization of containers, treatment device
2 container
3 radiation finger, casing
4 charge carrier emission window
5 projection
6 charge carrier cloud
7 medium line
8 arrow, interfering radiation
9 medium
10 arrow, residual radiation
11 inner wall
12 medium emission opening
R radiation direction of the charge carriers

The invention claimed is:

1. An apparatus for sterilization of an inner wall of containers using accelerated charge carriers comprising a charge carrier source for producing charge carriers, an acceleration device by which the charge carriers are accelerated in a direction of a charge carrier emission window, wherein the charge carrier emission window is arranged on a treatment device for introduction through an opening into the container along an insertion direction, to act upon an inner wall of the container with the charge carriers issuing from the charge carrier emission window, wherein the treatment device has a medium line with a medium emission opening, the medium emission opening of which is arranged for introduction through the opening into the container, wherein the treatment device has at least one projection which protrudes with respect to the charge carrier emission window in the insertion direction and which is suitable for absorbing interfering radiation, and wherein the medium line is arranged to have a medium flow for discharge through a medium emission opening at least into the region of the charge carriers issuing out of the charge carrier emission window, wherein the medium is suitable for changing a dimension of a charge carrier cloud formed by the issuing charge carriers.

2. The apparatus according to claim 1, wherein the medium is suitable for reducing a dimension of a charge carrier cloud formed by the issuing charge carriers, in such a way that interfering radiation is capable of being conveyed up to at least 25%, preferably at least 50%, preferably at least 60%, preferably at least 70%, preferably at least 80%, and in a particularly preferred manner at least 90%, to the projection protruding with respect to the charge carrier emission window and is capable of being absorbed by the aforesaid projection.

3. The apparatus according to claim 1, wherein the medium is suitable for changing at least one physical property, preferably the density, of a further medium arranged in the region of the charge carrier cloud formed by the issuing charge carriers.

4. The apparatus according to claim 1, wherein the medium line has a curved shape at least locally, wherein the medium line preferably is curved such that the medium being conveyed in it is discharged through the medium emission opening in the direction of the charge carrier cloud, preferably with a component in a direction opposed, and in a particularly preferred manner in a direction substantially opposed to an acceleration direction (R) of the charge carriers.

5. The apparatus according to claim 1, wherein the projection protruding with respect to the charge carrier emission window extends at least locally along a periphery of the treatment device, preferably around the entire periphery, in a particularly preferred manner in the form of a straight circular cylinder.

6. The apparatus for the sterilization of containers according to claim 1, wherein the medium line is connected at least locally to the treatment device, is preferably integrated in the latter and is movable jointly with the treatment device.

7. A plant for the treatment of containers wherein the plant has at least one apparatus for the sterilization of containers, preferably a plurality of apparatus for the sterilization of containers, as claimed in claim 1.

8. A plant for the treatment of containers as claimed in claim 7, wherein the plant has an insertion device for introducing a treatment device into the interior of a container, wherein the container and the treatment device are movable relative with respect to each other, preferably in a longitudinal direction of the container.

9. A method of sterilizing an inner wall of containers using accelerated charge carriers, wherein the charge carriers are produced in a charge carrier source and are accelerated with an acceleration device in a direction of a charge carrier emission window, wherein the charge carrier emission window is arranged on a treatment device which is introduced through an opening into the container along an insertion direction to act upon an inner wall of the container with the charge carriers issuing from the charge carrier emission window, wherein the treatment device has a medium line with a medium emission opening, the medium emission opening of which is arranged for introduction through the opening into the container, wherein the treatment device has at least one projection which protrudes with respect to the charge carrier emission window in the insertion direction and which can absorb radiation, and wherein the medium line is capable of having a medium flow through it for discharge through the medium emission opening at least into the region of the charge carriers issuing out of the charge carrier emission window, wherein the medium changes the dimension of a charge carrier cloud formed by the issuing charge carriers.

10. The method according to claim 9, wherein the medium discharged into the region of the charge carriers issuing out of the charge carrier emission window reduces a dimension of a charge carrier cloud formed by the issuing charge carriers, in such a way that interfering radiation is conveyed up to at least 25%, preferably at least 50%, preferably at least 60%, preferably at least 70%, preferably at least 80%, and in a particularly preferred manner at least 90%, to the projection protruding with respect to the charge carrier emission window and is capable of being absorbed by the aforesaid projection.

11. The method according to claim 9, wherein in the case of a reduction in the dimension of the charge carrier cloud formed by the issuing charge carriers by the medium, the intensity of the interfering radiation is reduced by the projection protruding with respect to the charge carrier emission window to a degree at which when changing the container to be sterilized it becomes superfluous to interrupt the acceleration of the charge carriers from the charge carrier source with the acceleration device in the direction of the charge carrier emission window.

12. The method according to claim 9, wherein the dimension of the charge carrier cloud is changed without switching off or changing a voltage of the acceleration device.

13. The method according to claim 9, wherein the dimension of the charge carrier cloud is reduced without switching off or changing a voltage of the acceleration device.

14. The method according to claim 9, wherein it is possible to change a geometry of the charge carrier cloud is changed without changing a power of the charge carrier source.

\* \* \* \* \*